United States Patent
Kroener et al.

(10) Patent No.: US 6,590,960 B2
(45) Date of Patent: Jul. 8, 2003

(54) COMPUTED TOMOGRAPHY APPARATUS WITH INTEGRATED UNBALANCED MASS DETECTION

(75) Inventors: Hans Juergen Kroener, Baiersdorf (DE); Hans-Juergen Mueller, Pretzeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/075,652

(22) Filed: Feb. 14, 2002

(65) Prior Publication Data

US 2002/0114424 A1 Aug. 22, 2002

(30) Foreign Application Priority Data

Feb. 20, 2001 (DE) .......................... 101 08 065

(51) Int. Cl.[7] .................. H05G 1/28; H05G 1/60; G01M 1/16; A61B 6/03
(52) U.S. Cl. .................. 378/162; 378/4; 378/15; 378/205; 378/207; 73/460; 73/462; 73/468; 73/470; 73/457; 73/458; 210/144; 494/10
(58) Field of Search .................. 378/4, 15, 162, 378/205, 207; 73/460, 462, 468, 470, 457, 458; 210/144; 494/1, 10

(56) References Cited

U.S. PATENT DOCUMENTS

| | | | | |
|---|---|---|---|---|
| 5,109,397 A | * | 4/1992 | Gordon et al. | 378/205 |
| 5,432,339 A | * | 7/1995 | Gordon et al. | 250/231.13 |
| 5,448,608 A | * | 9/1995 | Swain et al. | 378/4 |
| 5,610,968 A | | 3/1997 | Deucher et al. | 378/199 |
| 5,627,762 A | * | 5/1997 | Cameron et al. | 700/279 |
| 6,350,224 B1 | * | 2/2002 | Cordaro et al. | 494/7 |
| 6,412,345 B1 | * | 7/2002 | Murray et al. | 73/468 |

* cited by examiner

Primary Examiner—Drew A. Dunn
Assistant Examiner—Allen C. Ho
(74) Attorney, Agent, or Firm—Schiff Hardin & Waite

(57) ABSTRACT

A computed tomography apparatus has a gantry that is rotatable around a rotational axis and a detector permanently disposed relative to the gantry, for determining an unbalanced mass of the gantry and a calculating unit for calculating the location or locations at the gantry at which a weight or at which weights should be arranged for compensating the unbalanced mass.

10 Claims, 2 Drawing Sheets

COMPUTED TOMOGRAPHY APPARATUS WITH INTEGRATED UNBALANCED MASS DETECTION

BACKGROUND OF THE INVENTION

1. Field of the Invention

The invention is directed to a computed tomography apparatus of the type having with a gantry that is rotatable around a rotational axis and means for determining an unbalanced mass of the gantry.

2. Description of the Prior Art

A computed tomography apparatus of the above type is disclosed, for example, in U.S. Pat. No. 5,610,968. The computed tomography apparatus has a gantry mounted to be rotatable around a rotational axis and at which the components such as, for example, an X-ray source or a radiation detector that rotate around a patient under examination together with the gantry during operation of the gantry, are arranged. If the gantry has an unbalanced mass, i.e., a tumbling motion of the gantry radially and/or axially relative to its rotational axis, can lead to unsharp images produced with the computed tomography apparatus. The unbalanced mass of the gantry is therefore determined with a specific imbalance indicator during manufacture of the computed tomography apparatus, and the gantry is subsequently provided with one or more weights in order to compensate the unbalanced mass or at least reduce it within a suitable range of tolerance. Suitable imbalance indicators are offered, for example, by the Brüel & Kjaer Vibro company (Brüel & Kjaer Vibro GmbH, Landwehrstrasse 55, 64293 Darmstadt).

After a replacement of the components arranged at the gantry, a renewed balancing of the gantry is usually required. To that end, the balancing device must be brought to the location at which the computed tomography apparatus is located.

Such a balancing device, however, is relatively expensive and the operation thereof is relatively complicated, so that a renewed balancing after a replacement of one of the components arranged at the gantry can be relatively costly.

SUMMARY OF THE INVENTION

It is therefore an object of the invention to provide a computed tomography apparatus which allows for a simpler balancing of the gantry.

According to the invention, the object is achieved in a computed tomography apparatus having a gantry that is rotatable around a rotational axis, an imbalance detector for determining an unbalanced mass of the gantry, and a calculation unit for calculating the location or locations of the gantry at which a weight or weights should be arranged for compensating the unbalanced mass. The computed tomography apparatus thus has components integrated into the apparatus for determining an unbalanced mass of the gantry. As a result, no external balancing device needs to be brought to the location of the computed tomography apparatus after a replacement of components at the gantry. A complicated adjustment of the external balancing device is thus eliminated, so that errors in the balancing can be reduced and even a less skilled technician can reliably balance the gantry. Moreover, the detector integrated in the computed tomography apparatus for determining an unbalanced mass can be specifically adapted to the computed tomography apparatus in order to enable a more precise balancing. During maintenance, a technician normally does not have an external balancing device available for cost reasons. A further advantage of the inventive computed tomography apparatus is therefore that the technician can economically and dependably check the unbalanced mass of the gantry as well during the course of maintaining the computed tomography apparatus.

After the unbalanced mass of the gantry is determined with the detector, the calculating unit calculates the location or locations at the gantry where the weight or the weights should be arranged for compensating the unbalanced mass. These locations can, for example, be made visible with a monitor of a control computer of the computed tomography apparatus. A relatively simple identification of the locations for arranging the weights is thus achieved.

In a version of the invention, the detector for determining an unbalanced mass is a measurement sensor that acquires the vibration radially or axially relative to the rotational axis of the gantry. This collaborates with a position acquisition unit which detects the position of the gantry relative to a stationary part of the computed tomography apparatus that is likewise part of the detector for determining an unbalanced mass. When the measurement sensor acquires vibrations radially relative to the rotational axis, conclusions about the unbalanced mass of the gantry radially relative to the rotational axis can be made in a known way, on the basis of a linkage of the vibration radially relative to the rotational axis and the position of the gantry relative to the housing of the computed tomography apparatus. The acquisition of the vibration axially relative to the rotational axis in conjunction with the acquisition of the position of the gantry relative to the housing of the computed tomography apparatus, in contrast, allow conclusions to be made about an unbalanced mass of the gantry axially relative to the rotational axis.

In a preferred embodiment of the invention, the detector for determining an unbalanced mass include at least two measurement sensors that acquire the vibration radially and axially relative to the rotational axis of the gantry. Then the unbalanced mass of the gantry radially as well as axially relative to the rotational axis of the gantry can be determined. The measurement sensors can be arranged at the computed tomography apparatus so that, for example, one measurement sensor only acquires the vibration radially relative to the rotational axis and the other measurement sensor only acquires the vibration axially relative to the rotational axis.

Knowledge of the position of the gantry relative to the stationary housing of the computed tomography apparatus during the rotation of the gantry is necessary for the reconstruction of images produced with the apparatus. In a preferred embodiment of the invention therefore the detector for determining an unbalanced mass that includes a detector necessary for the acquisition of the position of the gantry relative to a stationary part of the computed tomography apparatus for the reconstruction of images produced with the computed tomography apparatus. The detector for position acquisition of the gantry relative to a stationary part of the computed tomography apparatus need be employed only once. As a result costs can be saved in the manufacture of the computed tomography apparatus.

In a further embodiment of the invention, the detector for determining an unbalanced mass of the gantry includes a computer that can be connected to an information transmission network, so that data representing an identified unbalanced mass of the gantry can be communicated to a central data bank. The central data bank, for example, can be operated by the manufacturer, a sales organization or a distribution organization for the computed tomography apparatus. It can also be operated by a service vendor who maintains the computed tomography apparatus. It is thus possible for the detector for determining an unbalanced mass of the gantry to check the unbalanced mass of the gantry automatically, for example every time when the computed tomography apparatus is in operation, in order to recognize a change in the unbalanced mass of the gantry. If, for example, the unbalanced mass of the gantry lies outside a prescribed tolerance range the computer can automatically contact the central data bank via the information transmission network. It is also possible for the computer to retain data that represent an unbalanced mass of the gantry and that lie beyond the range of tolerance in a memory of the computer, so that the manufacturer, the distribution organization, the sales organization or the service vendor regularly contacts the computer of the computed tomography apparatus via the information transmission network and uses the data bank to read out the memory of the computer. In both instances, thus, the manufacturer, the distribution organization, the sales organization or the service vendor is quickly informed about the modified unbalanced mass of the gantry, and accordingly can quickly dispatch a technician to the computed tomography apparatus in order to re-balance the gantry. The unbalanced mass of the gantry of a computed tomography apparatus that is operating is thus essentially continuously monitored.

In another version of the invention, the calculating unit for calculating the location or locations of the gantry is a control computer of the computed tomography apparatus. Beyond calculating those locations at which the weights should be arranged for balancing the gantry, the control computer controls the rotation of the gantry, the x-ray source and the radiation detector during the production of images of a patient with the computed tomography apparatus.

In a preferred embodiment of the invention, the calculating unit for calculating the location or locations of the gantry take locations into consideration at which components are arranged at the gantry. These components, for example, according to one version of the invention, are an x-ray source, a radiation detector and/or a cooling device for cooling an x-ray tube of the x-ray source. Obviously, no weights or balancing the gantry can be arranged at the locations at which components are already arranged. In known balancing devices, this fact is ignored and locations for arranging the weights are determined which may interfere with components already arranged on the gantry. In order to nonetheless balance the gantry, an experienced technician must find those locations on the basis of the locations determined by the balancing device at which there is still space for the weights. The precision of the balancing is thus dependent on the experience of the technician implementing the balancing. Even such a technician, who, however, must make a number of balancing attempts until the gantry is balanced within the prescribed tolerance range.

Since, inventively, the calculating unit for calculating the location or locations of weights takes into consideration the locations at which components are already arranged at the gantry, i.e. only determine those locations for the arrangement of the weights at the gantry where there is still space, the balancing can be quickly and relatively precisely implemented by a less experienced technician. The need for a number of balancing attempts is also eliminated, so that time and thus costs can be reduced.

DESCRIPTION OF THE PREFERRED EMBODIMENTS

Figure 1:
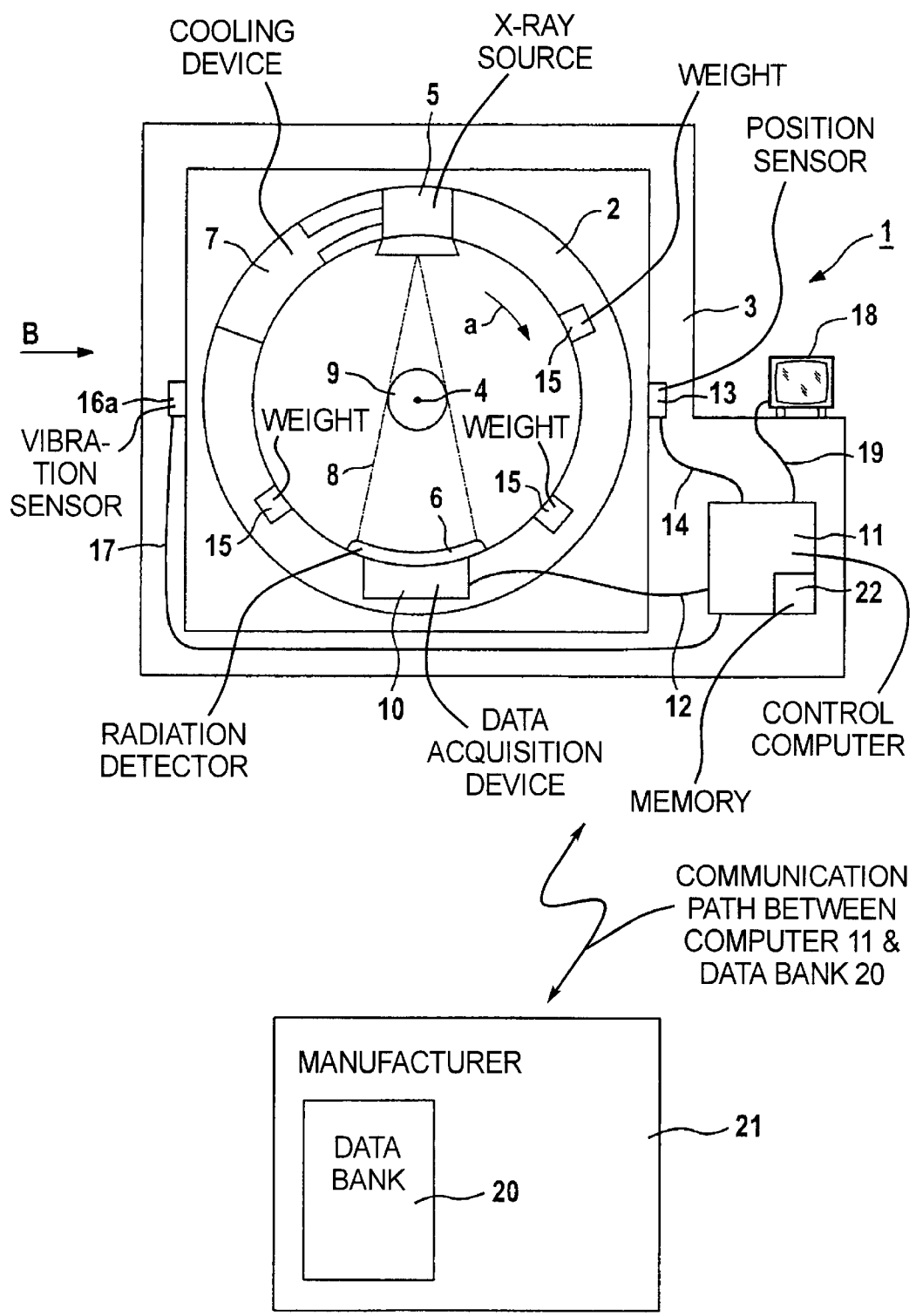
FIG. 1 is an end view of a computed tomography apparatus constructed and operating in accordance with the principles of the present invention, which can communicate with a data bank at a location remote from the computed tomography apparatus.
Figure 2:
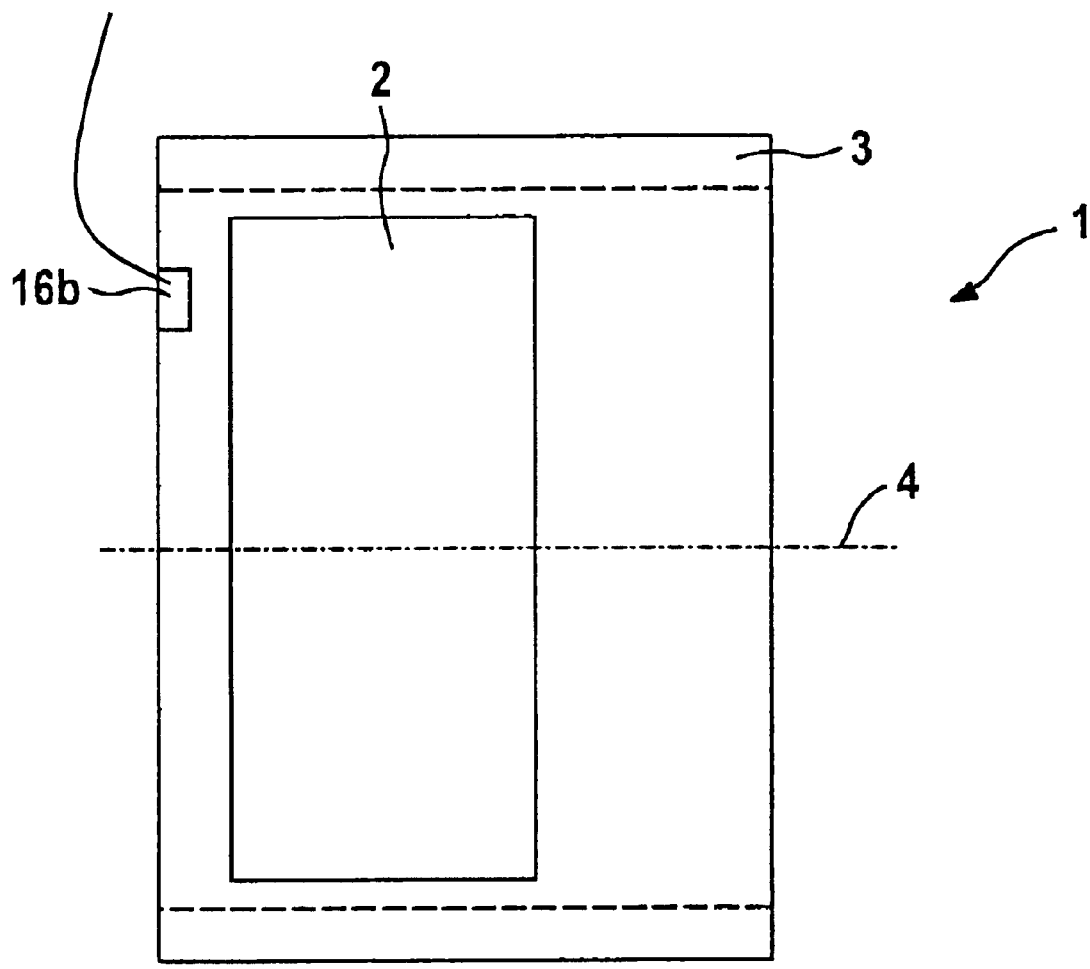
FIG. 2 is a side view of the computed tomography apparatus of FIG. 1.

As an example, FIG. 1 schematically shows a side view of a computed tomography apparatus 1 having an annularly fashioned gantry 2 that is mounted at a stationary housing 3 of the computed tomography apparatus 1 rotatable around a rotational axis 4 in the direction of the arrow 'a', aligned at a right angle relative to the plane of the drawing of FIG. 1. FIG. 2 schematically shows another side view of the computed tomography apparatus 1 shown in FIG. 1 in the direction of the arrow B shown in FIG. 1. The housing 3 of the computed tomography apparatus 1 is not shown in greater detail in the exemplary embodiment.

A number of components are arranged at the gantry 2. In the case present exemplary embodiment these are an x-ray source 5, a radiation detector 6 lying opposite the x-ray source 5 and a cooling device 7 (not shown in greater detail) for the elimination of heat that is generated by the x-ray tube of the x-ray source 5 during operation of the computed tomography apparatus 1. During operation of the computed tomography apparatus 1, the gantry 2 rotates around the rotational axis 4, and a fan-shaped x-ray beam 8 emanates from the x-ray source 5 and penetrates a measurement field 9 at different projection angles, and is incident on the radiation detector 6. A data acquisition device 10 acquires the resulting measured values from the output signals of the radiation detector 6, the measured values being supplied to a control computer 11 of the computed tomography apparatus 1. The control computer 11 uses these measured values to calculate an image of a patient located in the measurement field 9 and not shown in FIGS. 1 and 2. In the exemplary embodiment, the data acquisition system 10 is connected by an electrical line 12 to the control computer 11. The electrical line 12 can contain, for example, a wiper ring system and a wireless transmission link. The electrical terminals of the x-ray source 5 and the radiation detector 6 are also accomplished via wiper rings in a known way that is not shown.

In order to be able to reconstruct images from the measured values, a known position sensor 13 is arranged at the housing 3 of the computed tomography apparatus 1, which acquires the position of the gantry 2 relative to the housing 3 during operation of the gantry 2 and communicates this information to the control computer 11 with an electrical line 14.

During manufacture of the computed tomography apparatus 1, an unbalanced mass of the gantry 2 usually arises radially as well as axially relative to the rotational axis 4, so that the gantry 2 does not rotate exactly with respect to its rotational axis 4. A relatively large unbalanced mass, however, can lead to unsharp images produced with the computed tomography apparatus 1 or can lead to damage to the apparatus 1. In a generally known way, weights 15 are thereby arranged at the gantry 2, for compensating the unbalanced mass of the gantry 2 or at least reducing this to within a justifiable tolerance range.

In order to identify the unbalanced mass of the gantry 2 without weights 15 attached thereto, and thus to find the locations for the weights 15, a measurement sensor 16a shown in FIG. 1 and a measurement sensor 16b shown in FIG. 2 are integrated in the housing 3. The measurement sensor 16a shown in FIG. 1 acquires a vibration in the radial direction with respect to the rotational axis 4 resulting during the rotation of the gantry 2 around the rotational axis 4 due to the unbalanced mass of the gantry and communicates this information to the control computer 11 via an electrical line 17. The measurement sensor 16b shown in FIG. 2, in contrast, acquires a vibration in the axial direction with respect to the rotational axis 4 resulting during the rotation of the gantry 2 around the rotational axis 4 as a result of the unbalanced mass of the gantry 2 and likewise communicates this information to the control computer 11 with an electrical line that is not shown in FIGS. 1 and 2. During the rotation of the gantry 2, the position sensor 13 simultaneously acquires the position of the gantry 2 relative the housing 3, so that the control computer 11, using a computer program called during the determination of the unbalanced mass determines the unbalanced mass of the gantry 2 similar to an external balancing device.

On the basis of the identified unbalanced mass, the control computer 11 uses a further computer program—having a first computing step that is similar to a calculation of an external balancing device—calculates those locations at the gantry 2 at which the weights 15 having a suitable mass must be arranged in order to compensate the unbalanced mass of the gantry 2. In this first computing step, the entire gantry 2 forms the basis for the arrangement of the weights 15, i.e. locations at the gantry 2 can also be found on the basis of this first computing step that are already occupied by components such as the x-ray source 5, the radiation detector 6 and the cooling device 7 at which, thus, there is no space for weights 15.

In a second computing step that is based on the first computing step, the control computer 11 using the computer program determines those locations at the gantry 2 on the basis of a suitable interpolation method at which there is still space for an arrangement of the weights 15. In this second computing step, thus, those locations are taken into consideration at which components such as the x-ray source 5, the radiation receiver 6 and the cooling device 7 are already arranged at the gantry 2.

So that a technician can also recognize those locations at the gantry 2 at which the weights 15 are to be arranged, these locations are presented on a monitor 18 that is connected to the control computer 11 with an electrical line 19.

Given a replacement of the components such as x-ray source 5, radiation detector 6 or cooling device 7, a renewed unbalanced mass of the gantry 2 usually arises, so that the weights 15 must either be arranged at other locations of the gantry 2, further weights (not shown in FIGS. 1 and 2) must be employed or some of the weights 15 must be removed. To this end, the technician can call the above-described computer program of the control computer 11 in order to find those locations at the gantry 2 at which the weights 15 must be arranged so that the change in the unbalanced mass of the gantry 2 produced by the replacement of the components is compensated or reduced to a point that it lies within the predetermined tolerance range.

The computer program for determining an unbalanced mass of the gantry 2 in the case of the exemplary embodiment makes this determination every time the computed tomography apparatus 1 is in operation. If the unbalanced mass of the gantry 2 happens to have changed over the course of time and lies outside the tolerance range, the control computer 11 automatically contacts a central data bank 20 that is operated by the manufacturer 21 of the computed tomography apparatus 1 in the exemplary embodiment.

The control computer 11 contacts the data bank 20 by dialing into a telephone network (not shown in FIG. 1) in a known way and thus contacts the data bank 20 that is likewise connected to the telephone network.

After the control computer 11 has contacted the data bank 20, the control computer 11 communicates data to the data bank 20 that are allocated to the unbalanced mass of the gantry 2 that is outside the range of tolerance. The manufacturer 21 thus is informed of the unbalanced mass of the gantry 2 and can dispatch a technician to the computed tomography apparatus 1 so that this gantry 2 can be re-balanced.

In the case of an identified unbalanced mass of the gantry 2 that lies outside the tolerance range, it is also possible to store this information in a memory 22 of the control computer 11. The manufacturer 21 then can regularly contact the control computer 11 with the data bank 20 via the information transmission network and thus recognize when the gantry 2 exhibits an unbalanced mass that lies outside the tolerance range.

The manufacturer 21 need not necessarily regularly contact the control computer 11. The data bank 20 can be operated by other entities or persons. The information transmission network also need not necessarily be a telephone network, but be the Internet. A central data bank 20 is also not compulsory for the invention. It is also not necessary for the unit for calculating an unbalanced mass to automatically determine the unbalanced mass of the gantry every time when the computed tomography apparatus 1 is in operation.

It is also not necessary that the control computer 11 take locations at which components are already arranged at the gantry 2 into consideration for calculating locations at which the weights 15 are to be arranged.

Although it is advantageous for cost reasons to employ the position sensor 13 for the reconstruction of the images produced with the computed tomography apparatus for determining an unbalanced mass of the gantry 2 as well, this is not compulsory for the invention. A second, separate position sensor can be employed for that purpose.

The two measurement sensors 16a and 16b of the detector for determining an unbalanced mass of the gantry 2 alternatively can be arranged at the housing 3 of the computed tomography apparatus 1 so that they both acquire the vibration radially relative to the rotational axis 4. So that they can also acquire the vibration of the gantry 2 axially relative to the rotational axis 4, they must be arranged at the housing 3 of the gantry 2 axially offset relative to the rotational axis 4.

It is also possible for the detector to determine an unbalanced mass of the gantry 2 to have only a single measurement sensor. This can be arranged at the housing 3 of the computed tomography apparatus 1 so that it acquires the vibration radially or the vibration axially relative to the rotational axis 4. The detector for determining an unbalanced mass of the gantry 2, however, can have more than two measurement sensors.

The computer programs for determining an unbalanced mass and for calculating the locations at which the weights 15 should be arranged also need not necessarily be stored in the control computer 11. Alternatively, they can be stored in a separate assembly integrated in the computed tomography apparatus 1 or can be stored in a separate computer connectable to the computed tomography apparatus 1.

Further, other components can be arranged at the gantry 2 such as, for example, a high-voltage generator for the x-ray tube of the x-ray source 5 and the like.

The patient mentioned in the exemplary embodiment can be either a human being or an animal. The invention also can be an industrially employed computed tomography apparatus.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A computed tomography apparatus comprising:

a gantry rotatable around a rotational axis, said gantry having a mass;

a detector permanently disposed relative to said gantry for detecting a property of said gantry during rotation thereof indicative of said mass being unbalanced relative to said rotational axis, said detector generating a detector signal representing said property; and a calculating unit supplied with said detector signal which calculates at least one location at said gantry for placement of a weight to balance said mass relative to said rotational axis.

2. A computed tomography apparatus as claimed in claim 1 wherein said detector comprises a measurement sensor which measures at least one of radial vibrations of said gantry relative to said rotational axis and axial vibrations of said gantry relative to said rotational axis.

3. A computed tomography apparatus as claimed in claim 1 wherein said detector comprises a first sensor which senses radial vibrations of said gantry relative to said rotational axis and a second sensor which senses axial vibrations of said gantry relative to said rotational axis.

4. A computed tomography apparatus as claimed in claim 1 further comprising:

a stationary part;

an image reconstruction system which includes a position sensor for detecting a position of said gantry relative to said stationary part; and said detector comprising said position sensor.

5. A computed tomography apparatus as claimed in claim 1 wherein said calculating unit generates data including at least an indication that said mass is unbalanced, and wherein said computed tomography apparatus further comprises:

a data bank disposed at a location remote from said gantry; and said calculating unit being adapted to communicate with said data bank via an information transmission network to communicate said data to said data bank for storage in said data bank.

6. A computed tomography apparatus as claimed in claim 1 further comprising a control computer connected to said gantry for controlling at least the rotation of said gantry, said control computer comprising said calculating unit.

7. A computed tomography apparatus as claimed in claim 1 further comprising a plurality of gantry components mounted to said gantry at respective gantry component positions, and wherein said calculating unit takes said gantry component positions into account for determining said at least one position of said weight, so that said at least one position does not coincide with any of said gantry component positions.

8. A computed tomography apparatus as claimed in claim 7 wherein said gantry components comprise at least one of an X-ray source, a radiation detector, and a cooling device.

9. A computed tomography apparatus comprising:

a gantry mounted for rotation around a rotational axis;

at least one gantry component mounted to said gantry for co-rotation therewith, said at least one gantry component being selected from the group consisting of an X-ray source, a radiation detector and a cooling device, said gantry and said at least one gantry component having a combined mass;

a vibration detector permanently disposed relative to said gantry, said vibration detector being selected from the group consisting of a detector for radial vibrations of said gantry relative to said rotational axis and a detector for axial vibrations of said gantry relative to said rotational axis, said vibration detector generating a detector output representing vibrations detected by said vibration detector; and a calculating unit supplied with said detector output for detecting an imbalance of said combined mass and calculating a location at said gantry for placement of a weight to balance said imbalanced combined mass.

10. A computed tomography apparatus comprising:

a stationary part;

a gantry mounted to said stationary part for rotation relative to said stationary part around a rotational axis;

an X-ray source and a radiation detector mounted to said gantry for co-rotation therewith, said gantry, said X-ray source and said radiation detector having a combined mass, and said gantry having an opening therein adapted to receive an examination subject disposed between said X-ray source and said radiation detector, said radiation detector generating output signals dependent on radiation from said X-ray source, attenuated by said examination subject, incident on said radiation detector;

a position detector for detecting a position of said gantry relative to said stationary part and for generating a position signal representing said position;

an image reconstruction computer supplied with said output signals from said radiation detector and said position signal for generating an image of said examination subject; and a calculating unit supplied with said position signal for identifying therefrom an imbalance of said combined mass relative to send rotational axis and for calculating a location at said gantry for placement of a weight for balancing said imbalance of said combined mass.

* * * * *